(12) United States Patent
TenHuisen et al.

(10) Patent No.: US 6,916,321 B2
(45) Date of Patent: Jul. 12, 2005

(54) SELF-TAPPING RESORBABLE TWO-PIECE BONE SCREW

(75) Inventors: Kevor S. TenHuisen, Clinton, NJ (US); Victor F. Janas, Monroe Township, NJ (US); Kevin L. Cooper, Flemington, NJ (US); David W. Overaker, Annandale, NJ (US); J. Jenny Yuan, Neshanic Station, NJ (US)

(73) Assignee: Ethicon, Inc., Somerville, NJ (US)

( * ) Notice: Subject to any disclaimer, the term of this patent is extended or adjusted under 35 U.S.C. 154(b) by 481 days.

(21) Appl. No.: 09/969,779

(22) Filed: Sep. 28, 2001

(65) Prior Publication Data

US 2003/0065332 A1 Apr. 3, 2003

(51) Int. Cl.⁷ .............................................. A61B 17/58
(52) U.S. Cl. ........................................... 606/73; 606/77
(58) Field of Search .............................. 606/72, 73, 74, 606/76, 77, 79, 80

(56) References Cited

U.S. PATENT DOCUMENTS

| | | |
|---|---|---|
| 4,105,034 A | 8/1978 | Shalaby et al. |
| 4,130,639 A | 12/1978 | Shalaby et al. |
| 4,141,087 A | 2/1979 | Shalaby et al. |
| 4,205,399 A | 6/1980 | Shalaby et al. |
| 4,519,713 A | 5/1985 | Godsey et al. |
| 4,537,185 A | 8/1985 | Stednitz |
| 4,759,110 A | 7/1988 | Rieger et al. |
| 4,927,421 A | 5/1990 | Goble et al. |
| 4,950,270 A | 8/1990 | Bowman et al. |
| 5,030,048 A | 7/1991 | Massa |
| 5,057,110 A * | 10/1991 | Kranz et al. .................. 606/62 |
| 5,062,843 A | 11/1991 | Mahony, III |
| 5,152,790 A | 10/1992 | Rosenberg et al. |
| 5,156,616 A | 10/1992 | Meadows et al. |
| 5,169,400 A | 12/1992 | Muhling et al. |
| 5,348,026 A | 9/1994 | Davidson |
| 5,364,400 A | 11/1994 | Rego, Jr. et al. |
| 5,370,662 A | 12/1994 | Stone et al. |
| 5,443,482 A | 8/1995 | Stone et al. |
| 5,464,929 A | 11/1995 | Bezwada et al. |
| 5,470,334 A | 11/1995 | Ross et al. |
| 5,522,817 A * | 6/1996 | Sander et al. .................. 606/72 |
| 5,529,736 A | 6/1996 | Shalaby et al. |
| 5,571,139 A | 11/1996 | Jenkins, Jr. |
| 5,584,836 A | 12/1996 | Ballintyn et al. |
| 5,597,579 A | 1/1997 | Bezwada et al. |
| 5,618,552 A | 4/1997 | Bezwada et al. |
| 5,632,748 A | 5/1997 | Beck, Jr. et al. |
| 5,645,547 A | 7/1997 | Coleman |
| 5,645,850 A | 7/1997 | Bezwada et al. |

(Continued)

FOREIGN PATENT DOCUMENTS

| | | |
|---|---|---|
| EP | 0390613 | 10/1990 |
| EP | 0471334 | 2/1992 |
| EP | 0 502 698 A | 9/1992 |
| EP | 0502698 | 9/1992 |
| EP | 0913131 | 5/1999 |
| EP | 0916312 | 5/1999 |
| EP | 1 055 398 A | 11/2000 |

(Continued)

OTHER PUBLICATIONS

Rosen and Thies, The Cellular and Molecular Basis of Bone Formation and Repair, R.G. Landes Company, Texas, 1995, Chapter 1, pp. 1–41.

(Continued)

*Primary Examiner*—Ralph A. Lewis

(57) ABSTRACT

An orthopedic interference screw has a hard, self-threading front section and a bioabsorbable rear section. The two sections are conjoined and threaded such that the hard front section cuts threads into the bone and the softer rear section follows the threads into the bone. Preferably, the screw has an axial bore for matingly receiving a turning tool such as a hex wrench.

22 Claims, 3 Drawing Sheets

U.S. PATENT DOCUMENTS

| | | | |
|---|---|---|---|
| 5,695,497 | A | 12/1997 | Stahelin |
| 5,698,213 | A | 12/1997 | Jamiolkowski et al. |
| 5,711,669 | A | 1/1998 | Hurson |
| 5,743,914 | A | 4/1998 | Skiba |
| 5,810,821 | A * | 9/1998 | Vandewalle ............... 606/65 |
| 5,824,011 | A | 10/1998 | Stone et al. |
| 5,824,247 | A | 10/1998 | Tunc |
| 5,827,287 | A | 10/1998 | Tunc |
| 5,859,150 | A | 1/1999 | Jamiolkowski et al. |
| 5,928,236 | A | 7/1999 | Augagneur et al. |
| 5,964,783 | A | 10/1999 | Grafton et al. |
| 5,968,045 | A | 10/1999 | Frazier |
| 6,001,101 | A | 12/1999 | Augagneur et al. |
| 6,022,352 | A * | 2/2000 | Vandewalle ............... 606/73 |
| 6,096,060 | A | 8/2000 | Fitts et al. |
| 6,099,529 | A | 8/2000 | Gertzman et al. |
| 6,162,225 | A | 12/2000 | Gertzman et al. |
| 6,187,008 | B1 * | 2/2001 | Hamman ................... 606/72 |
| 6,423,062 | B2 * | 7/2002 | Enayati .................... 606/59 |
| 6,458,134 | B1 * | 10/2002 | Songer et al. ............. 606/73 |
| 6,471,707 | B1 * | 10/2002 | Miller et al. .............. 606/73 |
| 6,517,543 | B1 * | 2/2003 | Berrevoets et al. ........ 606/73 |
| 6,547,792 | B1 * | 4/2003 | Tsuji et al. ................ 606/72 |
| 6,565,291 | B2 | 5/2003 | Harpaz et al. |
| 2001/0034520 | A1 | 10/2001 | Enayati |

FOREIGN PATENT DOCUMENTS

| | | |
|---|---|---|
| FR | 2 720 627 A | 12/1995 |
| FR | 2 721 819 A | 1/1996 |
| JP | 07 213534 A | 8/1995 |
| JP | 1170126 | 3/1999 |
| WO | 9315682 | 8/1993 |
| WO | 9407425 | 4/1994 |
| WO | 9518577 | 7/1995 |
| WO | 9609014 | 3/1996 |
| WO | 9625104 | 8/1996 |
| WO | 9746167 | 12/1997 |
| WO | 9911177 | 3/1999 |
| WO | 0024324 | 5/2000 |
| WO | 0059389 | 10/2000 |

OTHER PUBLICATIONS

Feagin, Jr., J.A. (ed.), the Crucial Ligaments, Churchill Livingstone, Inc., New York, 1988, pp. 179–195 and 401–408.

Fu, F.H., et al., "Current Trends in Anterior Cruciate Ligament Reconstruction, Part 1: Biology and Biomechanics of Reconstruction", The American Journal of Sports Medicine, vol. 27, No. 6, American Orthopaedic Society for Sports Medicine, 1999, pp. 821–830.

Fu, F.H., et al., "Current Trends in Anterior Cruciate Ligament Reconstruction, Part 2: Operative Procedures and Clinical Correlations", The American Journal of Sports Medicine, vol. 28, No. 1, American Orthopaedic Society for Sports Medicine, 2000, pp. 124–130.

Jorge Heller, "Poly(ortho esters)", Handbook of Biodegradable Polymers, Harwood Academic Publishers, Netherlands, (1997), pp. 99–118.

John Kemnitzer, et al., "Degradable Polymers Derived from the Amino Acid L–Tyrosine", Handbook of Biodegradable Polymers, Harwood Academic Publishers, Netherlands, (1997), pp. 251–272.

J. Vandorpe, et al., "Biodegradable Polyphosphazenes for Biomedical Applications", Handbook of Biodegradable Polymers, Harwood Academic Publishers, Netherlands, (1997), pp. 161–182.

Allcock, et al., "Poly(phenylene Ether) to Radical Polymerization", Encyclopedia of Polymer Science and Engineering, vol. 13, John Wiley & Sons, Inc., New York (1988), pp. 31–41.

Daniel Cohn, et al., "Biodegradable PEO/PLA Block Copolymers", Journal of Biomedical Materials Research, vol. 22, John Wiley & Sons, Inc., (1988), pp. 993–1009.

D. Cohn, "New Tailor–Made Biodegradable Polymeric Biomaterials" Polymer Preprints, vol. 30, No. 1, Division of Polymer Chemistry, Inc., Dallas, Texas, (Apr. 1989), p. 498.

* cited by examiner

SELF-TAPPING RESORBABLE TWO-PIECE BONE SCREW

FIELD OF THE INVENTION

This invention relates to orthopedic screws and related surgical procedures using same, and, more particularly, to interference screws for securing synthetic or biological connective tissue to bone.

BACKGROUND OF THE INVENTION

The knee joint is one of the strongest joints in the body because of the powerful ligaments that bind the femur and tibia together. Although the structure of the knee provides one of the strongest joints of the body, the knee is usually one of the most frequently injured joints, e.g., athletes frequently stress and tear knee ligaments. The large number of ligament injuries has given rise to considerable innovative surgical procedures and devices for replacing and reconstructing torn or dislocated ligaments, typically involving grafting autografts, allografts, or a synthetic construct, to the site of a torn or dislocated ligament. For example, the replacement of an anterior cruciate ligament (ACL) may involve transplanting a portion of the patellar tendon, looped together portions of semitendinosus-gracilis (hamstring) tendons, or donor achilles tendons, to attachment sites in the region of the knee joint.

The most widely used technique for the reconstruction of the ACL is known as the Jones procedure. The basic steps in the procedure include: harvesting a graft made from a portion of the patellar tendon with attached bone blocks; preparing the graft attachment site (e.g., drilling holes in opposing bones of the joint in which the graft will be placed); placing the graft in the graft attachment site; and rigidly fixing the bone blocks in place within the graft site, i.e., the holes or "bone tunnels". The screws used to fix the graft in place are called "interference screws" because they are wedged between the bone block and the wall of the hole into which the bone block fits. Typically, there is very little space between the bone block and the hole in the bone at the fixation site.

Interference screws for anchoring ligaments to bone are typically fabricated from medically approved metallic materials that are not naturally absorbed by the body. A disadvantage of such screws is that once healing is complete, an additional surgical procedure may be required to remove the screw from the patient. Metallic screws may include a threaded shank joined to an enlarged head having a transverse slot or hexagonal socket formed therein to engage, respectively, a similarly configured, single blade or hexagonal rotatable driver for turning the screw into the bone. The enlarged heads on such screws can protrude from the bone tunnel and can cause chronic irritation and inflammation of surrounding body tissue.

Permanent metallic medical screws in movable joints can, in certain instances, cause abrading of ligaments during normal motion of the joint. Screws occasionally back out after insertion, protruding into surrounding tissue and causing discomfort. Furthermore, permanent metallic screws and fixation devices may shield the bone from beneficial stresses after healing. It has been shown that moderate periodic stress on bone tissue, such as the stress produced by exercise, helps to prevent decalcification of the bone. Under some conditions, the stress shielding which results from the long term use of metal bone fixation devices can lead to osteoporosis.

Biodegradable or bioabsorbable interference screws have been proposed to avoid the necessity of surgical removal after healing. Because the degradation of a biodegradable screw occurs over a period of time, support load is transferred gradually to the bone as it heals. This reduces potential stress shielding effects. Conventional bioabsorbable interference screws are softer and weaker than metallic compositions, such that they are not self-tapping, requiring the holes drilled into the bone to be tapped. The necessity to tap holes in the injured bone adds to the complexity of the surgical procedure and lengthens the time required to complete the operation.

Considerable effort has been expended to increase the stiffness and strength of bioabsorbable materials through various composite technologies, such as incorporating strong, stiff, non-absorbable, inorganic structural fibers or particles made from carbon or glass, as reinforcing agents in a bioabsorbable polymeric matrix. The disadvantage of this approach is that the non-absorbable fibers remain in the body tissue after the bioabsorbable polymer has been absorbed and may migrate or cause tissue inflammation. Composite bioabsorbable screws may also be prepared by incorporating inorganic, bioabsorbable glass or ceramic reinforcement fibers or particles in a bioabsorbable polymer matrix. However, lack of reinforcement-to-matrix interfacial bonding leads to poor load transfer between the reinforcement and the matrix. The weakness of the interface is accentuated when the implants are placed in the human body and may result in compromised long-term performance.

Reinforced bioabsorbable composite screws have also been made by adding an organic bioabsorbable reinforcing fiber to a bioabsorbable polymer matrix. Similarly, highly drawn fibers of polylactide (PLA) or polyglycolide (PGA) can be fused to form a bioabsorbable polymeric screw with increased stiffness and strength. Unfortunately, the consolidation or the melting temperature of the matrix usually causes the biocompatible organic fibers to partially relax their molecular orientation, thereby losing their strength and stiffness and adversely affecting the properties of the composite. Thus the efforts to utilize bioabsorbable materials for orthopedic load bearing applications has not been entirely successful.

Accordingly, there is a need for interference screws composed mainly of bioabsorbable materials that do not require tapped holes for insertion into bone.

SUMMARY OF THE INVENTION

The limitations of prior art interference screws are remedied by the present invention which includes an orthopedic screw for introduction into a bone tunnel. The screw has a first section having a first end forming a tip of the screw. The first section extends from the first end to an intermediate point along the length of the screw. The first section is formed from a first material and has external threads along at least a portion of its length. A second section of the screw extends from the intermediate point to a second end of the screw distal to the tip. The second section is formed from a bioabsorbable material and has external threads along at least a portion of the length thereof. The first section has a hardness such that the first section is self-threading when the first section is screwed into the bone tunnel.

DETAILED DESCRIPTION OF THE INVENTION

Figure 1:
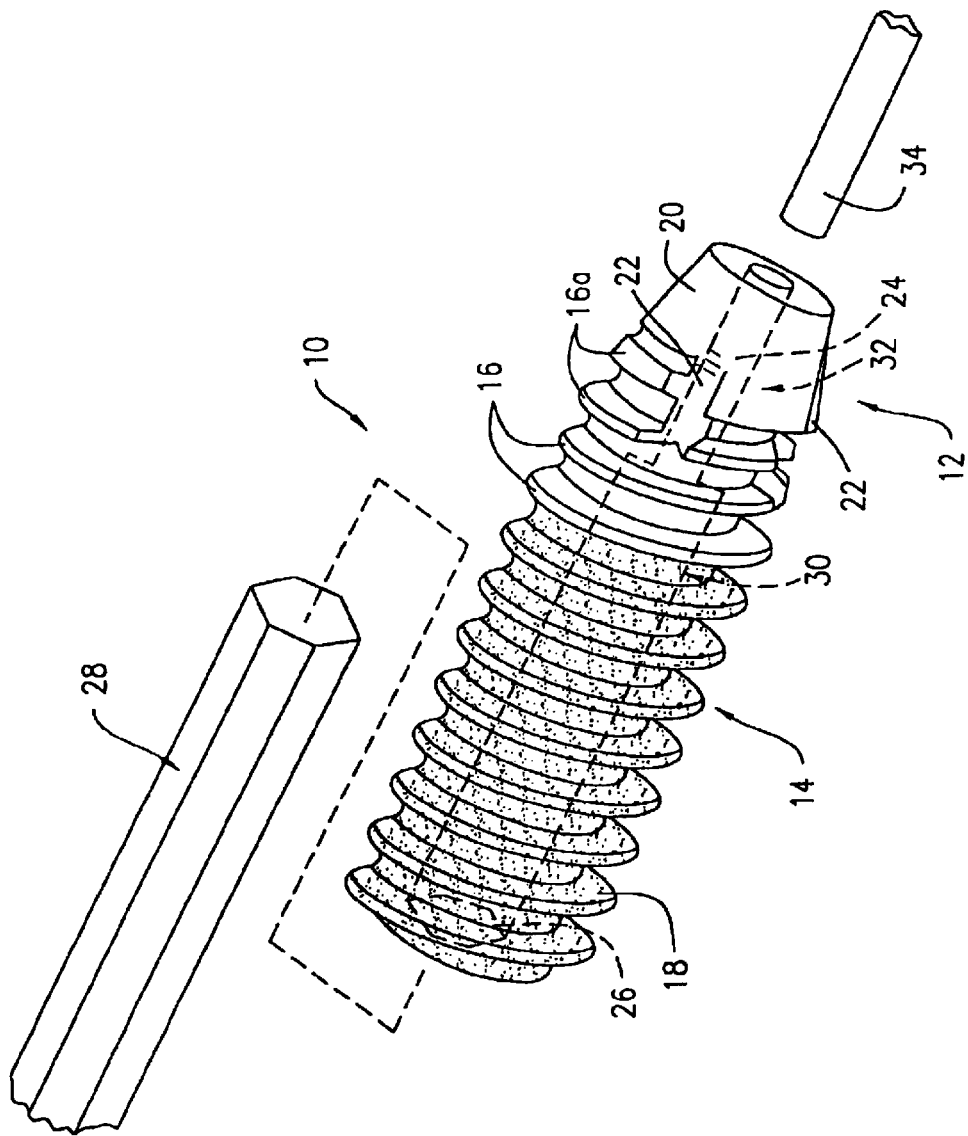
FIG. 1 is a perspective view of the device of an interference screw in accordance with a first exemplary embodiment of the present invention.

The present invention relates to an orthopedic surgical interference screw 10 for securing synthetic or biological connective tissue to a bone surface, such as, in the process of attaching and retaining a replacement anterior cruciate ligament (ACL) within a bone tunnel. The screw 10 has a front component/section 12 fabricated from a material with strength and hardness at least equivalent to that of bone, and a rear component/section 14 fabricated from a bioabsorbable polymer. Both front and rear components 12, 14 are externally threaded, i.e., with threads 16, 18, respectively, that are substantially continuous when the front and rear components 12, 14 are abutted together. The front component 12 has a tapered tip 20 with at least one and preferably a plurality of longitudinal flutes 22 to allow the front portion 12 to tap threads while being inserted into a hole in the bone. A tapered tip and flutes of this type are conventional on taps and self-threading screws. The threads 18 of the rear component 18 hold the screw 10 in place in the bone tunnel, as well as hold the bone blocks of the replacement anterior cruciate ligament (ACL) against the walls of the bone tunnels.

Both the front and rear components 12, 14 have axial bores 24, 26, respectively. The axial bore 26 of the rear component 14 is shaped to matingly receive a tool 28, such as a hex wrench. Although the tool 28 shown is hexagonal in shape, one skilled in the art could envision other axial bore 24, 26 shapes for receiving another tool shape. These include, but are not limited to, polygonal, cross, star, or oval shapes. The axial bore 24 of the front component 12 is stepped, with tool-shaped portion 30 proximate to the rear component 14 and a guide pin portion 32 proximate the tapered tip 20. When the front and rear components 12, 14 are assembled, the tool 28 may be inserted through the axial bore 26 and extend into the tool-shaped portion 30 of the axial bore 24. A guide pin 34 may be inserted into the guide pin portion 32 of the axial bore 24 in order to guide the screw 10 into the bone tunnel during an ACL reconstruction procedure. The taper of tip 20 extends over the threads 16a forming lead-in threads which cooperate with the flutes 22 to aid in self-threading. As noted above, threads 16 gradually transition to threads 18, i.e., they are of uniform pitch and are like-handed; that is, they share the same rotational direction of advancement.

Figure 2:
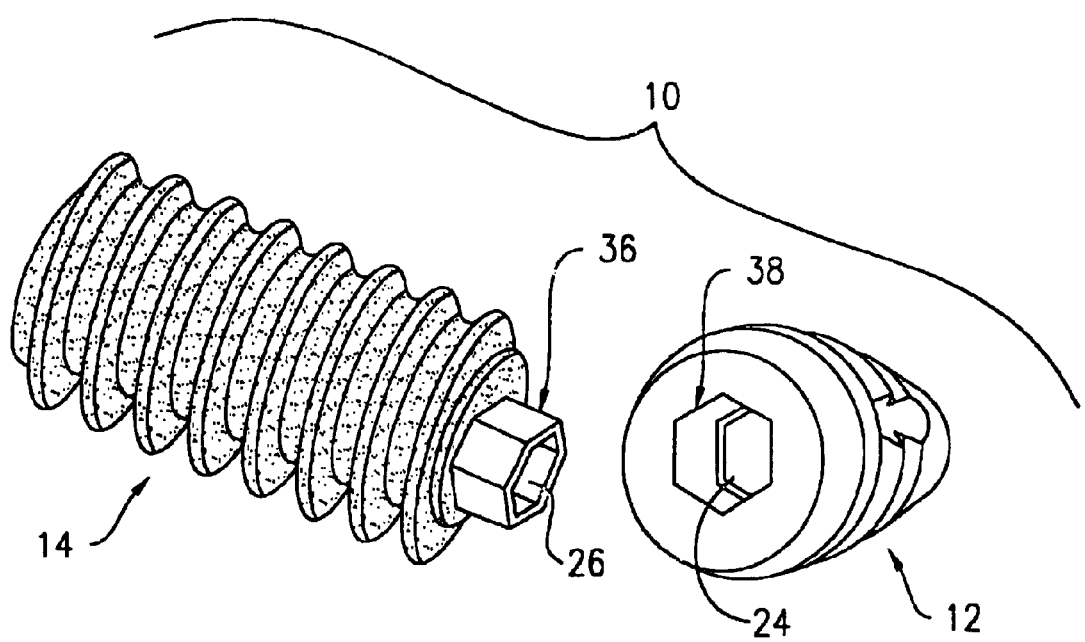
FIG. 2 is an exploded, perspective view of the screw of FIG. 1.

FIG. 2 shows that the screw 10 is provided with means for orienting and retaining the front component 12 in association with the rear portion 14. Namely, a hollow boss/projection 36 extends from the rear component 14 and is matingly received in a recess 38 provided in the front component 12. In FIG. 2, the external shape (hexagonal) of the boss 36 mimics the hexagonal shape of the axial bore 26. Similarly, the recess 38 has a hexagonal shape of somewhat greater dimensions than the tool-shaped portion 30 of the axial bore 24. The boss 36 may exhibit a friction fit relative to the recess 38 to retain the front and rear components 12, 14 together during handling and while being threaded into bone. Alternatively, the boss 36 and recess 38 may be provided with detents and mating depressions, threads, or other standard features used to fasten two pieces together in threaded, snap-fit, welded or glued relationship. The boss 36 could extend from the front component 12 and the recess be provided in the rear component 14.

Besides functioning as a means for attaching the front and rear components 12, 14, boss 36 also prevents relative rotation between front component 12 and rear component 14 in the event tool 28 is not inserted into tool-shaped portion 30 of the axial bore 24. Although boss 36 is shown as hexagonal in shape, one skilled in the art could envision boss 36 being other shapes, which prevent relative rotation between front component 12 and rear component 14. These include, but are not limited to, polygonal, cross, star, or oval shapes.

Figure 3:
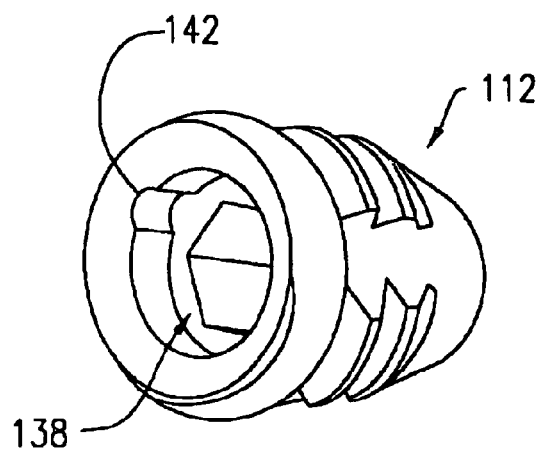
FIG. 3 is a perspective view of a front component of an interference screw of an alternative embodiment of the present invention.
Figure 4:
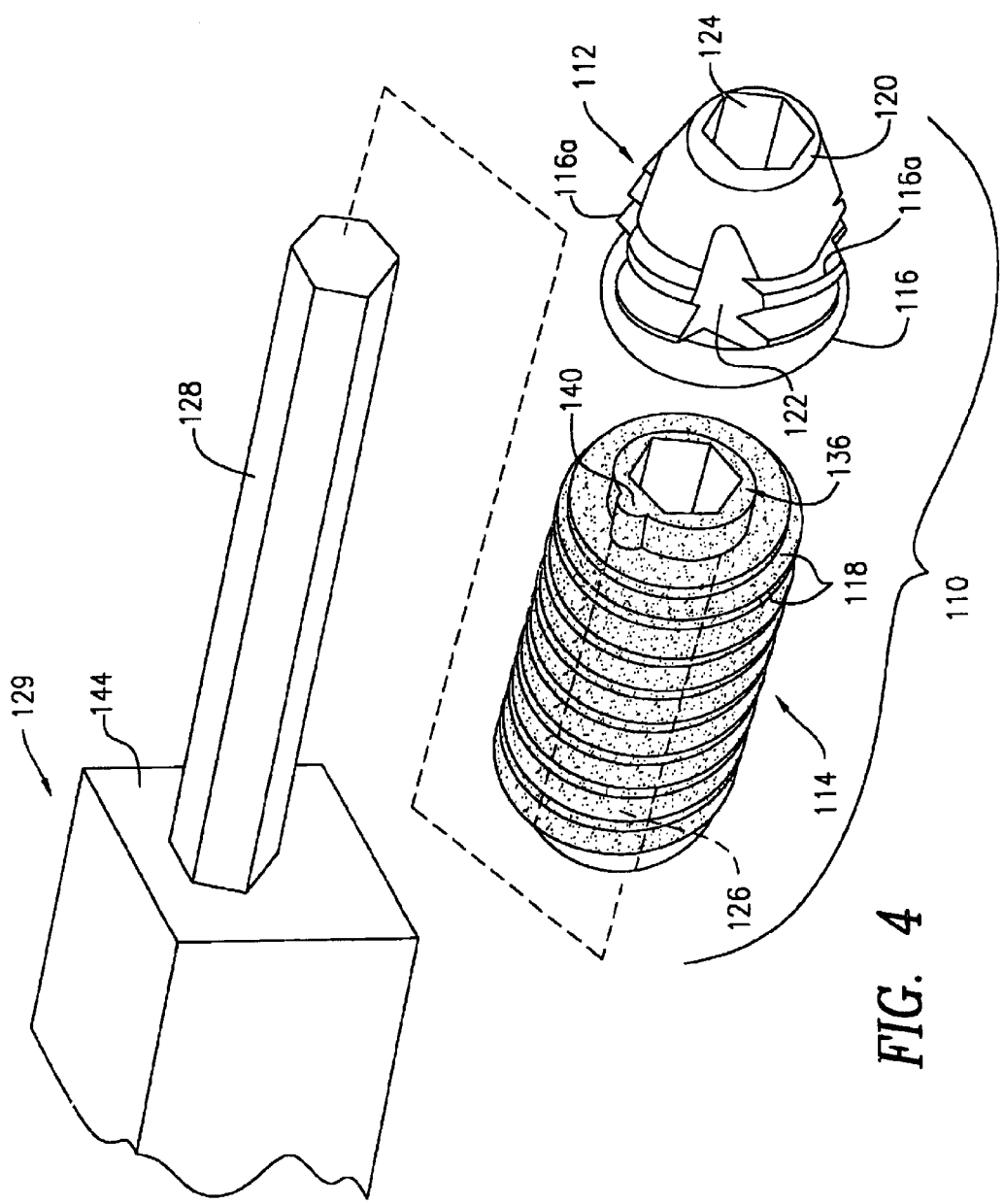
FIG. 4 is an exploded, perspective view of the screw having the front component shown in FIG. 3.

FIGS. 3 and 4 show an alternative embodiment 110 of the present invention wherein the boss 136 is in the form of a generally cylindrical collar having an alignment key 140. Elements illustrated in FIGS. 3 and 4, which correspond to elements described above with respect to FIGS. 1 and 2, have been designated by corresponding reference numerals increased by 100. The boss 136 inserts within a mating recess 138 in front component 112 (FIG. 3) with the alignment key 140 being received in a mating alignment slot 142. Due to the asymmetry of the alignment key 140, the front and rear components 112, 114 have a predetermined relative assembly orientation.

Unlike the axial bore 24 of the first embodiment 10, the axial bore 124 of the second embodiment 110 is not stepped, such that wrench portion 128 of tool 129 may extend through the axial bore 124 to the full length of the front component 112 to the tip 120 thereof. Wrench portion 128 preferably extends from an abutment surface 144 against which the rear component 114 abuts when the tool 129 is used to screw the screw 110 into bone. As with the insertion of self-threading fasteners generally, the insertion tool, e.g., 129 is pushed toward the substrate into which the fastener, e.g., 110 is to be inserted. Simultaneously, the tool, e.g. 129, is turned such that the threads, e.g., 116a, bite into the material, e.g., bone, and advance down into the material. With respect to the screw 110, the insertion pressure exerted on the tool 129 pushes the rear component 114 into engagement with the front component 112 insuring relative alignment and continuity of threads 116, 118.

In both of the foregoing embodiments 10, 110, a relatively hard front component 12, 112 with thread cutting features, viz., flutes 22, 122 and lead-in threads 16a, 116a does the thread cutting that permits a relatively soft bioabsorbable rear component 14, 114 conjoined to the front component 12, 112 to threadedly follow the front component 12, 112 into bone. For the purposes of retaining the screw 10, 110 in association with the insertion tool 28, 128, it is preferred that the tool 28, 128 has a friction-fit relative to the axial bores 24, 26, 124, 126, respectively.

The screws 10, 110 of the present invention can be used in the Jones procedure for the reconstruction of the ACL as follows. After the steps of harvesting and preparing the patellar tendon graft, preparing the graft site by drilling holes through the tibia and femur, and placing the graft within the drilled holes, the screws of the present invention are used to rigidly fix the upper and lower bone blocks in place within the holes. The screws of the present invention are placed between the bone blocks and the holes drilled in the femur and tibia. The screws 10, 110 of the present invention wedge themselves between the bone block and the wall of the hole at the graft attachment site. In the Jones procedure, first the femoral bone block is fixed with an interference screw. Then, with the knee almost straight, and with firm tension applied to the lower half of the graft using the sutures that were previously placed through the holes drilled in the lower (tibial) bone block, a second screw is placed up into the tibial drill hole from below.

As mentioned above, the screw 10, 110 of the present invention includes a front component 12, 112 formed from a material with strength and hardness at least equivalent to that of bone, and a rear component 14, 114 comprised of a bioabsorbable polymer. Suitable materials from which the rear component 14, 114 of the screw 10, 110 may be formed include biocompatible polymers selected from the group consisting of aliphatic polyesters, polyorthoesters, polyanhydrides, polycarbonates, polyurethanes, polyamides and polyalkylene oxides.

In the preferred embodiment, the rear component 14, 114 of the screw 10, 110 is formed from aliphatic polymers and copolymer polyesters and blends thereof. The aliphatic polyesters are typically synthesized in a ring opening polymerization. Suitable monomers include but are not limited to lactic acid, lactide (including L-, D-, meso and D,L mixtures), glycolic acid, glycolide, ε-caprolactone, p-dioxanone (1,4-dioxan-2-one), trimethylene carbonate (1,3-dioxan-2-one), δ-valerolactone, β-butyrolactone, ε-decalactone, 2,5-diketomorpholine, pivalolactone, α,α-diethylpropiolactone, ethylene carbonate, ethylene oxalate, 3-methyl-1,4-dioxane-2,5-dione, 3,3-diethyl-1,4-dioxan-2,5-dione, gamma-butyrolactone, 1,4-dioxepan-2-one, 1,5-dioxepan-2-one, 6,6-dimethyl-dioxepan-2-one, 6,8-dioxabicycloctane-7-one and combinations thereof. These monomers generally are polymerized in the presence of an organometallic catalyst and an initiator at elevated temperatures. The organometallic catalyst is preferably tin based, e.g., stannous octoate, and is present in the monomer mixture at a molar ratio of monomer to catalyst ranging from about 10,000/1 to about 100,000/1. The initiator is typically an alkanol (including diols and polyols), a glycol, a hydroxyacid, or an amine, and is present in the monomer mixture at a molar ratio of monomer to initiator ranging from about 100/1 to about 5000/1. The polymerization typically is carried out at a temperature range from about 80° C. to about 240° C., preferably from about 100° C. to about 220° C., until the desired molecular weight and viscosity are achieved.

Suitable materials for forming the front component 12, 112 include, but are not limited to, biocompatible metals such as stainless steel and cobalt-chrome alloys, glasses or ceramics.

Preferably, the materials comprising the front component 12, 112 of the screw 10, 110 will be absorbable. Suitable absorbable materials comprising the front component 12, 112 include, but are not limited to, glasses or ceramics comprising mono-, di-, tri-, α-tri-, β-tri-, and tetra-calcium phosphate, hydroxyapatite, calcium sulfates, calcium oxides, calcium carbonates, magnesium calcium phosphates, phospate glasses, bioglasses, mixtures thereof or a stiff, strong polymer, such as a polyglycolic acid polymer. The front component of the present invention can also be formed from autograft, allograft, or xenograft bone tissues.

The front component 12, 112 of the screw 10, 110 further can be made from combinations of metals, absorbable ceramics, glasses and polymers. In a preferred embodiment, the front component of the screw may be comprised of composites prepared by incorporating bioabsorbable glass or ceramic reinforcements such as fibers or particles in a bioabsorbable polymer matrix. The lack of fiber to matrix interfacial bonding leading to compromised long-term performance when the composite is implanted, which was discussed earlier, is avoided because once the front component 12, 112 taps the screw thread, the rear component 14, 114 bears the load of holding the bone block against the wall of the hole into which the bone block fits.

In another embodiment of the present invention, the polymers, polymer blends, or composites can be used as a therapeutic agent release matrix. To form this matrix, the polymer would be mixed with a therapeutic agent prior to forming the front or rear components 12, 14 of the screw. The variety of different therapeutic agents that can be used in conjunction with the polymers of the present invention is vast. In general, therapeutic agents which may be administered via the pharmaceutical compositions of the invention include, without limitation: antiinfectives such as antibiotics and antiviral agents; chemotherapeutic agents (i.e. anticancer agents); anti-rejection agents; analgesics and analgesic combinations; anti-inflammatory agents; hormones such as steroids; growth factors, including bone morphogenic proteins (i.e. BMP's 1–7), bone morphogenic-like proteins (i.e. GFD-5, GFD-7 and GFD-8), epidermal growth factor (EGF), fibroblast growth factor (i.e. FGF 1–9), platelet derived growth factor (PDGF), insulin like growth factor (IGF-I and IGF-II), transforming growth factors (i.e. TGF-β I–III), vascular endothelial growth factor (VEGF); and other naturally derived or genetically engineered proteins, polysaccharides, glycoproteins, or lipoproteins. These growth factors are described in *The Cellular and Molecular Basis of Bone Formation and Repair* by Vicki Rosen and R. Scott Thies, published by R. G. Landes Company (1994), hereby incorporated herein by reference.

Matrix materials for the present invention may be formulated by mixing one or more therapeutic agents with the polymer. Alternatively, a therapeutic agent could be coated on to the polymer, preferably with a pharmaceutically acceptable carrier. Any pharmaceutical carrier can be used that does not dissolve the polymer.

The therapeutic agent may be present as a liquid, a finely divided solid, or any other appropriate physical form. Typically, but optionally, the matrix will include one or more additives, such as diluents, carriers, excipients, stabilizers or the like. The amount of therapeutic agent will depend on the particular drug being employed and medical condition being treated. Typically, the amount of drug represents about 0.001 percent to about 70 percent, more typically about 0.001 percent to about 50 percent, most typically about 0.001 percent to about 20 percent by weight of the matrix. The quantity and type of polymer incorporated into the drug delivery matrix will vary depending on the release profile desired and the amount of drug employed.

Upon contact with body fluids, the polymer undergoes gradual degradation (mainly through hydrolysis) with concomitant release of the dispersed drug for a sustained or extended period. This can result in prolonged delivery (over, say 1 to 5,000 hours, preferably 2 to 800 hours) of effective amounts (say, 0.0001 mg/kg/hour to 10 mg/kg/hour) of the drug. This dosage form can be administered as is necessary depending on the subject being treated, the severity of the affliction, the judgment of the prescribing physician, and the like. Following this or similar procedures, those skilled in the art will be able to prepare a variety of formulations.

The following example is illustrative of the principles and practice of this invention, although not limited thereto.

Numerous additional embodiments within the scope and spirit of the invention will become apparent to those skilled in the art.

EXAMPLE 1

Three screws were made for simulation of a bone-tendon-bone ACL repair. Two of the screws were controls. The controls were monolithic in nature, i.e. composed of a single material, and of a one-piece design which incorporated all of the features of the present invention except for the means of connecting a front and rear component.

The first control was composed of poly(lactic acid), or PLA, machined from billets of PLA previously formed by injection molding. The second control was composed of a composite of 20/80 (volume percent) β-tricalcium phosphate (TCP) particles (10-micron average diameter) in PLA. These screws were also machined from billets of TCP/PLA composites previously formed by injection molding.

The third screw included a front and rear component. The rear component was composed of PLA machined from the same billets of PLA formed by injection molding as mentioned above. The front component was composed of metal machined from the rods of cold rolled stainless steel. The front and rear components were press fit to form a two-piece screw.

Fresh frozen porcine knees were used for simulation of a bone-tendon-bone ACL repair. After thawing, the femur was securely clamped and the patella was dissected free from its proximal attachment. An 11-mm diameter patellar bone plug, attached to the patellar tendon, was harvested. The plug was fashioned with a Stryker 11-mm bone plug cutter and the patella tendon was dissected free at its tibial attachment.

A 13-mm diameter bone tunnel was prepared by overdrilling a guide pin placed at the ACL origin and exteriorizing on the side of the femoral condyle. The bone plug was placed into the tunnel until its end protruded two to three millimeters out of its proximal end. Since the bone plug was 11-mm in diameter and the tunnel was 13-mm in diameter, there existed a 2-mm gap into which attempts were made to drive each screw into the gap. A standard hexagonal driver was used to attempt driving the screws through the cortical side of the bone plug.

The PLA control screw could not be driven into the bone tunnel/bone plug gap. The composite control screw was successfully driven into the bone tunnel/bone plug gap. During the insertion process, this screw exerted considerable resistance to torsion and a "biting" sound could be heard, suggesting that the entire length of the threads were cutting into bone. The two-piece prototype easily self-tapped, with the relatively small number of threads on the stainless steel front component biting into and cutting the bone, and the softer, polymer rear component following the front component with minimal friction resistance.

What is claimed is:

1. An orthopedic screw for introduction into a bone tunnel, comprising:
   a first section having a first end forming a tip of said screw, said first section extending from said first end to an intermediate point along the length of said screw, said first section including external threads along at least a portion of the length thereof, and said first section being made from a first material having a hardness such that said first section is self-threading when said first section is screwed into the bone tunnel; and
   a second section coupled to said first section and extending from said intermediate point to a second end of said screw distal to said tip, said second section being formed from a bioabsorbable material which is different than said first material and said second section including external threads along at least a portion of the length thereof.

2. The screw of claim 1, further including a projection extending from one of said first section and said second section to the other of said first section and said second section to be received in a mating recess provided therein to conjoin said first section and said second section.

3. The screw of claim 2, wherein said projection is a hexagonal boss and said recess is a mating hexagonal recess.

4. The screw of claim 2, wherein said projection is asymmetric and said recess is matingly asymmetric establishing a single assembly orientation of said first section relative to said second section.

5. The screw of claim 4, wherein said projection is substantially cylindrical with at least one radially extending side prominence.

6. The screw of claim 1, further including an axial bore extending through said second section for at least a portion of the length thereof, said bore matingly receiving a tool for applying a turning force to said screw.

7. The screw of claim 6, wherein said axial bore is hexagonal along a portion of its length, said hexagonal portion being a tool receiving portion for receiving a hex wrench therein.

8. The screw of claim 6, wherein said axial bore extends through the entire length of said screw from said first end to said second end.

9. The screw of claim 8, wherein said axial bore proximate said first end has a shape for matingly receiving a guide pin.

10. The screw of claim 1, wherein said threads of said first section and said threads of said second section are continuous relative to one another when said first section is conjoined to said second section and have the same direction of rotational advancement.

11. The screw of claim 10, wherein said first end is tapered to aid in introducing said screw into a hole in bone.

12. The screw of claim 11, wherein said first end has at least one longitudinal flute cutting across at least one of said threads in said first section.

13. The screw of claim 12, wherein at least one of said threads on said first section is a starter thread.

14. The screw of claim 1, wherein said first section is bioabsorbable.

15. The screw of claim 14, wherein said first section is made from a material selected from the group consisting of mono-, di-, tri-, α-tri, β-tri, and tetracalcium phosphate, hydroxyapatite, calcium sulfates, calcium oxides, calcium carbonates, magnesium calcium phosphates, phosphate glasses, bioglasses, mixtures thereof, polyglycolic acid polymers and bone tissues.

16. The screw of claim 1, wherein said first section is made from a material selected from the group consisting of stainless steel, cobalt-chrome alloys, glasses, ceramics and polymers.

17. The screw of claim 1, wherein said second section is made from a material selected from the group consisting of aliphatic polyesters, polyorthoesters, polyanhydrides, polycarbonates, polyurethanes, polyamides and polyalkylene oxides.

18. The screw of claim 1, wherein said first section is conjoined to said second section by gluing.

19. The screw of claim 1, wherein said first section is conjoined to said second section by welding.

20. A two-piece interference screw, comprising:
 a front section made from biocompatible material with a strength and hardness equivalent to that of bone; and
 a rear section made from a bioabsorbable polymer and coupled to said front section.

21. The screw of claim 20, wherein said front section is bioabsorbable.

22. A method for securing a bone plug in a bone hole using a two-piece interference screw, comprises the steps of:
 providing a front screw section composed of biocompatible material having strength and hardness at least equivalent to that of bone;
 providing a rear screw section composed of bioabsorbable polymer;
 coupling the front screw section to the rear screw section thereby forming the interference screw;
 placing a tip of the interference screw into the bone hole;
 turning the interference screw while simultaneously urging the interference screw into the bone hole;
 cutting threads into the bone hole with the front screw section; and
 permitting the rear screw section to thread into the threads cut by the front screw section.

* * * * *